US005728399A

United States Patent [19]
Wu et al.

[11] Patent Number: 5,728,399
[45] Date of Patent: Mar. 17, 1998

[54] USE OF A BACTERIAL COMPONENT TO ENHANCE TARGETED DELIVERY OF POLYNUCLEOTIDES TO CELLS

[75] Inventors: George Y. Wu; Catherine H. Wu, both of Avon; Ying Zhang, Farmington; George L. Spitalny, Cheshire; Ellen Carmichael, West Hartford, all of Conn.

[73] Assignees: University of Conn., Storrs, Conn.; TargeTech, Inc. a wholly owned subsidiary of The Immune Response Corporation, Carlsbad, Calif.

[21] Appl. No.: 484,009

[22] Filed: Jun. 7, 1995

Related U.S. Application Data

[63] Continuation-in-part of Ser. No. 267,710, Jun. 29, 1994, abandoned.

[51] Int. Cl.$^6$ .................................................. A61K 9/127
[52] U.S. Cl. ...................... 424/450; 435/199; 435/320.1; 536/24.1; 536/25.1
[58] Field of Search ............................ 536/23.5, 24.1, 536/25.1; 424/450; 530/350; 514/44; 435/172.3, 320.1, 199

[56] References Cited

U.S. PATENT DOCUMENTS

| | | | |
|---|---|---|---|
| 5,135,736 | 8/1992 | Anderson et al. | 424/1.49 |
| 5,166,320 | 11/1992 | Wu et al. | 530/395 |
| 5,169,933 | 12/1992 | Anderson et al. | 530/391.3 |
| 5,354,844 | 10/1994 | Beug et al. | 530/345 |

FOREIGN PATENT DOCUMENTS

| | | |
|---|---|---|
| WO 92/06180 | 4/1992 | WIPO . |
| WO 92/19749 | 11/1992 | WIPO . |
| WO 92/20316 | 11/1992 | WIPO . |
| WO 92/22635 | 12/1992 | WIPO . |
| WO 93/04701 | 3/1993 | WIPO . |
| WO 94/06922 | 3/1994 | WIPO . |
| WO 94/06923 | 3/1994 | WIPO . |

OTHER PUBLICATIONS

Orkin et al., *Report and Recommendations of the Panel to Assess the NIH Investment in Research on Gene Therapy*, 1995, NIH.

Jeljasewicz, J. and Wadstrom, T., *Bacterial Toxins and Cell Membranes*, Chapter 5, pp. 129–183, Academic Press (1978).

Cumber et al. (1985), "[16] Preparation of Antibody–Toxin Conjugates", *Methods In Enzymology*, vol. 112, pp. 207–225.

Cotten et al. (1992), "High–Efficiency Receptor–Mediated Delivery Of Small And Large (48 Kilobase Gene Constructs Using The Endosome–Disruption Activity Of Defective Or Chemically Inactivated Adenovirus Particles", *Proc. Natl. Acad. Sci. USA*, vol. 89, pp. 6094–6098.

Curiel et al. (1991), "Adenovirus Enhancement Of Transferrin–Polylysine–Mediated Gene Delivery", *Proc. Natl. Acad. Sci. USA*, vol. 88, pp. 8850–8854.

Curiel et al. (1992), "Gene Transfer To Respiratory Epithelial Cells Via The Receptor–Mediated Endocytosis Pathway", *Amer. Journ. of Respiratory and Molecular Bio.*, vol. 6, pp. 247–252.

Wu et al. (1991), "Delivery Systems For Gene Therapy", *Biotherapy*, vol. 3, pp. 87–95.

Wagner et al. (1992), "Coupling Of Adenovirus To Transferrin–Polylysine/DNA Complexes Greatly Enhances Receptor–Mediated Gene Delivery And Expression Of Transfected Genes", *Proc. Natl. Acad. Sci. USA*, vol. 89, pp. 6099–6103.

Wagner et al. (1992), "Influenza Virus Hemagglutinin HA-2 N–Terminal Fusogenic Peptides Augment Gene Transfer By Transferrin–Polylysine–DNA Complexes: Toward A Synthetic Virus–Like Gene–Transfer Vehicle", *Proc. Natl. Acad. Sci. USA*, vol. 89, pp. 7934–7938.

Wagner et al. (1990), "Transferrin–Polycation Conjugates As Carriers For DNA Uptake Into Cells", *Proc. Natl. Acad. Sci. USA*, vol. 87, pp. 3410–3414.

Alouf, J.E., Fehrenbach, F.J., Freer, J.H., and Jeljaszewicz, J., *Bacterial Protein Toxins*, pp. 165–171, Academic Press (1984).

Geoffroy et al. (1987), "Purification, Characterization, And Toxicity Of The Sulfhydryl–Activatd Hemolysin Listeriolysin O From *Listeria monocytogenes*", *Infection And Immunity*, vol. 55, pp. 1641–1646.

Zenke et al. (1990), "Receptor–Mediated Endocytosis Of Transferrin–Polycation Conjugates: An Efficient Way To Introduce DNA Into Hematopoietic Cells", *Proc. Natl. Acad. Sci. USA*, vol. 87, pp. 3655–3659.

Portnoy et al. (1992), "Capacity Of Listeriolysin O, Streptolysin O, And Perfringolysin O To Mediate Growth Of *Bacillus subtilis* Within Mammalian Cells", *Infection and Immunity*, vol. 60, pp. 2710–2717.

Wilson et al. (1992), "Hepatocyte–Directed Gene Transfer In Vivo Leads To Transient Improvement of Hypercholesterolemia In Low Density Lipoprotein Receptor–Deficient Rabbits", *The Journ. of Biol. Chem.*, vol. 267, pp. 963–967.

Prigent et al. (1976), "Interaction Of Streptolysin O Wityh Sterols", *Biochimica et Biophysica Acta*, vol. 443, pp. 288–300.

(List continued on next page.)

*Primary Examiner*—James Ketter
*Attorney, Agent, or Firm*—Jane E. Remillard; Lahive & Cockfield, LLP

[57] ABSTRACT

An improved soluble molecular complex for targeting a polynucleotide to a specific cell is disclosed. The molecular complex comprises (a) a polynucleotide (b) a carrier made up of a polynucleotide binding agent and a cell-specific binding agent which binds to a surface molecule of the cell and is internalized into an endosome, and (c) a bacterial component or fragment thereof which lyses the endosome and causes the polynucleotide to be released into the cytoplasm of the cell. In a preferred embodiment of the invention the polynucleotide binding agent is polylysine, the cell-specific binding agent is an asialoglycoprotein, and the bacterial component is listeriolysin O. The disclosed soluble molecular complex and methods of use can be used therapeutically to deliver genes and antisense polynucleotides to specific cells in vivo.

16 Claims, No Drawings

OTHER PUBLICATIONS

Cristiano et al., (1993), "Hepatic Gene Therapy: Adenovirus Enhancement Of Receptor–Mediated Gene Delivery And Expression in Primary Hepatocytes", *Proc. Natl. Acad. Sci. USA*, vol. 90, pp. 2122–2126.

Wu et al., (1987), "Receptor–Mediated In Vitro Gene Transformation By a Soluble DNA Carrier System", *The Journ. of Biol. Chem.*, vol. 262, pp. 4429–4432.

Wu et al., (1988), "Receptor–Mediated Gene Delivery And Expression In Vivo", *The Journ. of Biol. Chem.*, vol. 263, pp. 14621–14624.

Wu et al., (1989), "Targeting Genes: Delivery And Persistent Expression Of A Foreign Gene Driven By Mammalian Regulatory Elements In Vivo", *The Journ. of Biol. Chem.*, vol. 264, pp. 16985–16987.

Barry, E.L.R. et al., (1993) "Introduction of Antisense Oligonucleotides into Cells by Permeabilization with Streptolysin O", *Biotechniques*, vol. 15, pp. 1018–1020.

Planck, C. et al., (1994) "The Influence of Endosome–Disruptive Peptides on Gene Transfer Using Synthetic Virus–Like Gene Transfer Systems", *The Journal of the Biological Chemistry*, vol. 269, pp. 12918–12924.

USE OF A BACTERIAL COMPONENT TO ENHANCE TARGETED DELIVERY OF POLYNUCLEOTIDES TO CELLS

RELATED APPLICATIONS

This application is a continuation-in-part of U.S. application Ser. No. 08/267,710, filed Jun. 29, 1994, now abandoned.

GOVERNMENT SUPPORT

The work that led to this invention was supported by one or more grants from the United States Government.

BACKGROUND OF THE INVENTION

Rapid development in molecular biology has shown the potential of using gene therapy to correct hereditary disorders by the introduction of normal functioning genes into human tissue. Many techniques for gene delivery in vitro have been developed in the past few years. Among these are calcium phosphate precipitation (Gopal (1985) *Mol Cell Biol.* 5:1188; Graham et al. (1973) *Virology* 52:456), electroporation (Potter et al. (1984) *PNAS* 81:7161), microinjection (Harland et.al. (,1985) *Cell Biol.* 101:1094), liposomes (Fraley et al. (1979) *PNAS* 76:3348) and retrovirus vectors (Guild et al. (1988) *Virology* 62:3795). However, intrinsic limitations have prevented some of these techniques from being widely used for in in vivo gene delivery. For example, retrovirus vectors will only integrate into dividing cells and there is a size limit for the foreign gene that the vector can carry. In calcium phosphate precipitation, plasma membrane damage occurs.

Recently, a soluble DNA targeting system has been developed for delivering DNA specifically to hepatocytes and other cells (Wu et al. *J. Biol. Chem.* (1987) 262:4429; U.S. Pat. No. 5,166,320). For delivery to hepatocytes, this system takes advantage of the receptor-mediated endocytosis of asialoglycoproteins by receptors highly selective for parenchymal liver cells. A soluble targetable conjugate has been developed consisting of a cell surface receptor-binding entity, asialoorosomucoid (ASOR) and a DNA-binding entity, polylysine. Polylysine binds DNA in a strong, nondamaging electrostatic manner and protects the DNA from nuclease attack. This conjugate can be targeted specifically to asialoglycoprotein receptor- bearing cells, resulting in cellular uptake and expression of foreign genes. (U.S. Pat. No: 5,166,320; Wilson et al. *J. Biol Chem.* (1992) 267:963; Wu et al. *J. Biol. Chem.* (1989) 242:16985; Wu et al. *Biochemistry* (1988) 27(3):887; Wu et al. *J. Biol. Chem.* (1991)266:14438).

Several approaches have been reported to enhance expression of delivered genes. For example, Curiel et al. recently reported enhanced gene expression by cotransfecting cells with intact adenovirus and a transferrin-polylysine-DNA complex (Curiel et al. (1991) *PNAS* 88:8850). Wagner et al. included certain fusogenic peptides derived from the N-terminal sequence of the influenza virus hemagglutinin as part of a DNA complex, resulting in a substantial augmentation of the transferrin-polylysine-mediated gene transfer (Wagner et al. (1992) PNAS 89:7934).

Additional methods for enhancing expression of transfected genes would be beneficial.

SUMMARY OF THE INVENTION

This invention pertains to an improved soluble molecular complex for targeting a polynucleotide to a specific cell for selective cellular internalization and to methods of using the molecular complex. The soluble molecular complex includes a polynucleotide complexed with a carrier component comprised of polynucleotide binding agent and a cell-specific binding agent which binds to a surface molecule of a cell and is internalized into an endosome. The complex further includes a bacterial component or portion thereof which is capable of lysing an endosome resulting in release of the polynucleotide into the cytoplasm of the cell.

The polynucleotide binding agent is a compound such as a polycation which stably complexes a polynucleotide under extracellular conditions and releases the polynucleotide under intracellular conditions in functional form. To prepare a carrier, the polynucleotide binding agent is linked to a cell-specific binding agent which binds a cellular surface structure, typically a cellular surface receptor, which mediates internalization of bound ligands by endocytosis into cellular endosomes. The cell-specific binding agent can be a natural or synthetic ligand (e.g., a protein, polypeptide, glycoprotein, carbohydrate, etc.) or it can be an antibody, or an analogue thereof, which specifically binds a cellular surface structure which then mediates internalization of the bound complex. A preferred target for the cell-specific binding agent is the asialoglycoprotein receptor of hepatocytes which binds to and mediates the internalization of galactose-terminal (asialo-) glycoproteins.

To enhance delivery of a polynucleotide to a cell, a bacterial component or active fragment thereof capable of lysing a cellular endosome is included in the molecular complex. Following internalization of the complex into an endosome of the cell, the bacterial component lyses the endosome resulting in release of the polynucleotide into the cytoplasm. Preferably, the bacterial component is pH dependent and is activated upon internalization into an endosome. Alternatively, the bacterial component is thiol-activated. A particularly preferred bacterial component is listeriolysin O, or active component thereof.

The soluble molecular complex of this invention can be used therapeutically to deliver polynucleotides, such as genes and antisense polynucleotides, to specific cells in vivo, in vitro, or ex vivo.

DETAILED DESCRIPTION OF THE INVENTION

This invention is based, at least in part, on the discovery that a bacterial component having the capacity to cause lysis of a cellular endosome can be used to enhance delivery of a polynucleotide to a specific cell. Accordingly, to enhance delivery of a polynucleotide into a cell via receptor mediated endocytosis, a bacterial component capable of lysing an endosome is included in a soluble molecular complex. The term "bacterial component", as used herein, includes any part of a bacterium or any substance produced by a bacterium which has the ability to lyse a cellular endosome, including proteins and fragments or analogies thereof having endosomolytic activity.

A soluble molecular complex of the invention includes a polynucleotide noncovalently linked to a carrier comprised of a polynucleotide binding agent and a cell-specific binding agent. The molecular complex further includes a bacterial component or fragment thereof which lyses a cellular endosome. The bacterial component can be linked to a component of the carrier, such as a polynucleotide binding agent. Alternatively, the bacterial component can be separately linked to a second polynucleotide binding agent and complexed with the remaining components of the molecular complex. As part of the molecular complex, the bacterial component or fragment thereof is internalized into the cell with the remaining components of the molecular complex (i.e., the polynucleotide, the polynucleotide binding agent, and the cell-specific binding agent) via the same endocytotic pathway. The cointernalized bacterial component or active fragment thereof causes lysis of the endosome, thereby releasing the components of the complex into the cytoplasm of the cell, resulting in increased uptake and/or prolonged activity of functional polynucleotide in the cell.

The polynucleotide to be delivered can be DNA, RNA or an analogue thereof. For example, targeted polynucleotides can be genes encoding desired proteins, such as secretory proteins (see U.S. patent application Ser. No. 710,558, filed on Jun. 5, 1991, and Ser. No. 893,736, filed on Jun. 5, 1992), such as clotting factors and other blood proteins; cell surface proteins (see U.S. patent application Ser. No. 695,598, filed on May 3, 1991), such as cell surface receptors for low density lipoproteins, for growth factors, or for hormones; immunogenic proteins (see U.S. patent application Ser. No. 699,891, filed on May 14, 1991, and Ser. No. 882,669, filed on May 14, 1992), such as vital proteins (e.g., hepatitis B surface antigen or HIV envelope proteins) or protein of other pathogens.

A polynucleotide encoding a desired protein is in a form suitable for expression by the target cell. For example, the polynucleotide can be a gene encoding appropriate signal sequences which provide for trafficking to intracellular destinations or cellular secretion of the product. The signal sequence may be the natural sequence of the protein or an exogenous sequence. The gene is operably linked to appropriate genetic regulatory elements required for expression of the gene product by the target cell. Regulatory sequences are art-recognized and are selected to direct expression of the desired protein in an appropriate cell. Accordingly, the term "regulatory sequence", as used herein, includes promoters, enhancers and other expression control elements. Such regulatory sequences are known and discussed in Goeddel, *Gene expression Technology: Methods in Enzymology*, p. 185, Academic Press, San Diego, CA (1990). The gene can be contained in an expression vector such as a plasmid or a transposable genetic element along with the genetic regulatory elements necessary for expression of the gene and secretion of the gene-encoded product.

Alternatively, the targeted polynucleotide can be an antisense polynucleotide (see U.S. patent application Ser. No. 07/941,368, filed on Sep. 4, 1992, and Ser. No. 08/042,943, filed on Apr. 5, 1993, and Ser. No. 08/181,557, filed Jan. 12, 1994). In other cases, the polynucleotide can be a gene encoding an RNA molecule which has catalytic activity, such as a ribozyme (see U.S. patent application Ser. No. 08/222,615, filed on Apr. 4, 1994). The molecular complex can contain more than one copy of the same polynucleotide or one or more different polynucleotide.

The carrier component of the complex is typically a conjugate of a cell-specific binding agent and a polynucleotide-binding agent. The cell-specific binding agent is an agent which targets the complex to a particular cell and which specifically binds a cellular surface structure which mediates its internalization into cellular endosomes by, for example, the process of endocytosis. The target surface structure for the binding agent can be a protein, polypeptide, carbohydrate, lipid or combination thereof. Typically, the cellular surface structure is a surface receptor which mediates endocytosis of a ligand. Thus, the binding agent can be a natural or synthetic ligand which binds the receptor. The ligand can be a protein, polypeptide, glycoprotein, glycopeptide or glycolipid which has functional groups that are exposed sufficiently to be recognized by the cell surface structure. It can also be a component of a biological organism such as a virus, or a cell (e.g., mammalian, bacterial, protozoan). The cell-specific ligand can also be an antibody, or an analogue of an antibody such as a single chain antibody, which binds the cell surface structure.

Ligands useful in forming the carrier will vary according to the particular cell to be targeted. For targeting hepatocytes, galactose-terminal carbohydrates such as carbohydrate trees obtained from natural glycoproteins, especially structures that either contain terminal galactose residues or can be enzymatically treated to expose terminal galactose residues, can be used. Alternatively, other ligands such as polypeptide hormones can be employed. In addition, naturally occurring plant carbohydrates such as arabinogalactan can be used as ligands. Other useful ligands for hepatocyte targeting include glycoproteins having exposed terminal carbohydrate groups such as asialoglycoproteins (galactose-terminal). These galactose-terminal ligands can be formed by coupling galactose-terminal carbohydrates such as lactose or arabinogalactan to nongalactose-bearing proteins by reductive lactosamination. Examples of additional asialoglycoproteins include, but are not limited to, asialoorosomucoid, asialofetuin and desialylated vesicular stomatitis virus. Such ligands can be formed by chemical or enzymatic desialylation of glycoproteins that possess terminal sialic acid and penultimate galactose residues.

For targeting the soluble molecular complex to other cell surface receptors, other types of ligands can be used, such as mannose for macrophages (lymphoran), mannose 6-phosphate glycoproteins for fibroblasts (fibro- sarcoma), intrinsic factor-vitamin B12 and bile acids (See Kramer et al. (1992) *J. Biol. Chem.* 267:18598–18604) for enterocytes, insulin for fat cells, and transferrin for smooth muscle cells or other cells bearing transferrin receptors. Alternatively, the cell-specific binding agent can be a receptor or a receptor-like molecule, such as an antibody which binds a ligand (e.g., antigen) on the cell surface. Such antibodies can be produced by standard procedures.

The polynucleotide-binding agent of the carrier complexes the polynucleotide to be delivered. Complexation with the polynucleotide must be sufficiently stable (either in vivo, ex vivo, or in vitro) to prevent significant uncoupling of the polynucleotide extracellularly prior to internalization by the target cell. However, the complex is cleavable under appropriate conditions within the cell so that the polynucleotide is released in functional form within the cell.

In a preferred embodiment, the binding between the polynucleotide-binding agent and the polynucleotide is based on electrostatic attraction which provides sufficient extracellular stability, but is releasable intracellularly. Preferred polynucleotide-binding agents are polycations that bind negatively charged polynucleotides. These positively charged proteins can bind noncovalently with the polynucleotide to form a targetable molecular complex which is stable extracellularly but releasable intracellularly. Suitable polycations are polylysine, polyarginine, polyornithine, basic proteins such as histones, avidin, protamines and the like. A preferred polycation is polylysine (e.g., ranging from 3,800 to 60,000 daltons). Other noncovalent bonds that can be used to releasably link the expressible polynucleotide include hydrogen bonding, hydrophobic bonding, electrostatic bonding alone or in combination such as, anti-polynucleotide antibodies bound to polynucleotide, and streptavidin or avidin binding to polynucleotide-containing biotinylated nucleotides.

Preferred polynucleotide-binding agents are polycations. These positively charged materials can bind noncovalently with the negatively charged polynucleotide to form a soluble, targetable molecular complex which is stable extracellularly but releasable intracellularly. Suitable polycations are polylysine, polyarginine, polyornithine, basic proteins such as histones, avidin, protarnines and the like. A preferred polycation is polylysine (e.g., ranging from 3,800 to 60,000 daltons). Other noncovalent bonds that can be used to releasably link the polynucleotide include hydrogen bonding, hydrophobic bonding, electrostatic bonding alone or in combination such as, anti-polynucleotide antibodies bound to polynucleotide, and strepavidin or avidin binding polynucleotide containing biotinylated nucleotides.

To enhance delivery of a polynucleotide to a cell, a bacterial component or fragment thereof capable of lysing cellular endosomes is included in the molecular complex. The bacterial component or fragment is typically covalently linked, preferably by a disulfide bond, to at least one of the carrier components, such as a polynucleotide binding agent. Alternatively, the bacterial component or fragment is separately linked to a second polynucleotide binding agent or a second cell-specific binding agent and complexed with the remaining components of the molecular complex.

In a preferred embodiment of the invention, the bacterial protein or peptide used in the molecular complex is activated upon internalization into a cellular endosome. The term "activated", as used herein, means that the bacterial component or portion thereof is able to lyse the endosome (e.g., by undergoing a conformational change, causing it to bind to the endosomal membrane and lyse the endosome). For example, the activity of the bacterial component can be pH dependent, i.e., the bacterial component has endosomolytic activity at the acidic pH within an endosome, but not at the pH outside the endosome (i.e., in the cell cytoplasm or outside the cell). Such a bacterial component is inactive extracellularly and will not harm a target cell or host when outside the cell or when released into the cytoplasm, but will become active after being exposed to the acidic environment inside an endosome of the cell.

In another preferred embodiment of the invention, the bacterial component is thiol-activated. Thiol-activated bacterial components are produced by various gram positive bacteria, including, but not limited to, bacteria of the families Bacillus, Streptococcus, Clostridium, Lactobacillus, and Listeria (see e.g., Smyth, C. J. and Duncan, J. L., *Bacterial Toxins and Cell Memebranes*, Chapter 5, p.129, Academic Press (1978); Alouf, J. E. and Geoffrey, C., *Bacterial component Toxins*, p.165, Academic Press (1984)). A thiol-activated bacterial component is one which contains one or more sulfhydryl groups which, when reduced, activate the protein and, when oxidized, inactivate the protein. In one embodiment, a thiol-activated bacterial protein, such as LLO, or a fragment of the protein which has reduced immunogenicity as compared to the whole protein, is linked to a carrier via the protein's free sulfhydryl group(s), thereby preventing reduction of the sulfhydryl group(s) and inhibiting activation of the protein. This configuration provides the advantage of preventing the bacterial protein or peptide from harming the target cell prior to internalization into an endosome of the cell. Once inside a cellular endosome, it is believed that the disulfide linkage between the bacterial protein and the carrier is reduced and the protein is released from the carrier in an active form, causing lysis of the endosome.

In a particularly preferred embodiment of the invention, the molecular complex includes the bacterial component Listeriolysin O (LLO), a 56 kD thiol-activated protein produced by *Listeria monocytogenes* or, even more preferably, a fragment of LLO which maintains endosomolytic activity yet has reduced immunogenicity, such as those described below in Example 3. LLO is fully active at pH 5.5, but loses most of its activity at pH 7 (see e.g., Portnoy et al. (1992) *Infection & Immunity* 60:2710). Therefore, as part of the molecular complex of the invention, it is believed that LLO is inactive extracellularly or in the cell cytoplasm at neutral pH and becomes active when the complex is internalized into the acidic environment of an endosome. Thus, LLO is particularly preferred for use in a molecular complex of the invention due to its lack of cytolytic activity ensuring little damage to the membrane of the cell when LLO is contacted with the cell extracellularly. Following entry into an endosome, it is believed that an active LLO binds to the membrane of the endosome and that such binding disrupts the permeability of the membrane, leading to lysis of the endosome.

Other pH dependent or thiol-activated bacterial components, such as pneumolysin, can also be included in the molecular complexes of the invention.

To produce a molecular complex of the invention, a carrier is formed by chemically coupling, preferably by a covalent interaction, a polynucleotide binding agent (e.g., polynucleotide) and a cell-specific binding agent (e.g., ASOR).

In one embodiment, the carrier is linked to a bacterial protein or fragment thereof capable of lysing on endosome.

In another embodiment, a conjugate of the bacterial component or fragment and the polynucleotide binding agent is prepared. Then, both that conjugate and the carrier are complexed with the polynucleotide. The resulting molecular complex includes a bacterial component which is linked separately to a polynucleotide binding agent and noncovalently complexed with the remaining components of the complex (i.e., the carrier and the polynucleotide).

The carrier can be formed by chemically linking the cell-specific binding agent to the polynucleotide-binding agent. The chemical linkage is typically covalent. A preferred linkage is a peptide bond. This can be formed with a water soluble carbodiimide as described by Jung, G. et al. (1981) *Biochem. Biophys. Res. Commun.* 101:599–606. Alternative linkages are disulfide bonds or strong noncovalent linkages as in avidin-biotin coupling.

The chemical linkage can be optimized for the particular cell-specific binding agent and polynucleotide-binding agent used to form the carrier. Reaction conditions can be designed to maximize linkage formation but to minimize the formation of aggregates of the carrier components. The optimal ratio of cell-specific binding agent to polynucleotide-binding agent can be determined empirically. When polycations are used, the ratio of the components will vary with the size of the polycation and the size of the polynucleotide. In general, this ratio ranges from about 10:1 to 1:1, preferably about 3:1 by weight. Uncoupled components and aggregates can be separated from the carrier by molecular sieve or ion exchange chromatography (e.g., Aquapore™ cation exchange, Rainin).

In one embodiment, asialoorosomucoid-polylysine conjugate is formed with the cross-linking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column (see U.S. patent application Ser. No.08/043,008, filed Apr. 5, 1993, the teachings of which are incorporated by reference herein).

According to one method for forming the molecular complex, the carrier and the bacterial component are linked. A preferred linkage is a disulfide bond. As described in the examples below, this linkage can be achieved using, for example a chemical cross linker such as N-Succinimidyl 3-(2-pyridyldithio)propionate (SPDP). Other cross-linking reagents which can be used include, for example, N-hydroxysuccinimidyl esters, N-Succinimidyl-(4-Iodoacetyl)aminobenzoate) (SIAB), Sulfo-SIAB, Sulfo-succinimidyl-4-maleimidophenyl-butyrate (Sulfo-SMPB), and water-soluble carbodiimides such as 1-ethyl-3-(3-dimethylaminopropyl)carbodiimide hydrochloride (EDC) (see e.g., Grabarek et al. (1990) Anal. Biochem. 185:131).

When using a thiol activated bacterial component, such as LLO, the carrier component can be thiolated using, for example, SPDP, and then linked directly to free sulfhydryl groups contained on LLO or peptides derived from LLO (see e.g., Cumber et al. (1985) Meth Enzymol 112:207). Linking LLO or peptides thereof to the carrier via its sulfaydryl groups can provide the advantage of ensuring that these thiol groups remain oxidized and that the activity of the LLO is inhibited while the complex is outside the target cell.

Following coupling of the carrier and a bacterial component, the resulting conjugate (carrier-bacterial component conjugate) is noncovalently complexed with a polynucleotide to via the polynucleotide binding agent. This can be achieved by a stepwise dialysis procedure. In one embodiment, for use with carriers made of polycations such as polylysine, the dialysis procedure begins with a 2 M NaCl dialyzate and ends with a 0.15 M solution. The gradually decreasing NaCl concentrations result in binding of the polynucleotide to the carrier-bacterial component conjugate. In some instances, particularly when concentrations of the polynucleotide and conjugate are low, dialysis may not be necessary; the polynucleotide and conjugate are simply mixed and incubated at room temperature for approximately 30 minutes.

The optimal ratio of polynucleotide to carrier-bacterial component conjugate for formation of a soluble molecular complex of the invention can range depending upon the type and size of the polynucleotide and the carrier-bacterial component conjugate used. For example, the molar ratio for oligonucleotides and carrier-protein conjugates made up of ASOR, polylysine, and LLO can range from about 1000:1 to about 10:1 (oligonucleotide to carrier-protein conjugate). The ratio can be determined for a particular polynucleotide and carrier-bacterial component conjugate by gel retardation assay as described in U.S. Pat. No. 5,166,320, the teachings of which are incorporated by reference herein. In brief, the proportion of polynucleotide to carrier-bacterial component conjugate which completely retards the migration of DNA run on a polyacrylamide gel is taken as the optimal ratio for complex formation.

According to a second method for forming a molecular complex of the invention, a conjugate of a bacterial component or fragment thereof capable of lysing endosomes and a polynucleotide binding agent or a cell specific binding agent (e.g., anti-cell surface receptor antibody) is formed. As an illustrative example, a bacterial component, such as LLO or a fragment of LLO having endosomolytic activity, is linked to a polynucleotide-binding agent (e.g. polynucleotide) using a chemical cross-linking reagents such as SIAB, Sulfo-SIAB, Sulfo-SMPB or EDC.

Alternatively, the bacterial component or portion thereof can be coupled with the polynucleotide binding agent enzymatically through the action of an enzyme such as transglutaminase or biochemically such as through a biotin-streptavidin bridge. The resulting conjugate can then be separated from free bacterial component and free polynucleotide binding agent by molecular sieve or ion exchange chromatography (e.g., Aquapore™ cation exchange, Rainin) using standard techniques.

In a particularly preferred embodiment, a polynucleotide binding agent-bacterial component conjugate is produced with LLO or, even more preferably, a fragment of LLO having endosomolytic activity, and polylysine by linking free sulfhydryl groups or free carboxyl groups contained on LLO to the polylysine. For example, polylysine can be thiolated using SPDP and then coupled directly to free sulfhydryl groups on LLO or peptides of LLO. Coupling can be achieved by incubation at room temperature for approximately 18 hours.

Following formation of a polynucleotide binding agent-bacterial component conjugate, the conjugate is noncovalently complexed with the remaining components of the molecular complex (i.e., the carrier made up of a polynucleotide-binding agent and cell-specific binding agent and formed as described above) by incubation at room temperature. For optimal complex formation, the polynucleotide should first be mixed with the carrier in an amount which only partially saturates the negative charge of the polynucleotide (i.e., approximately one-forth of the negative charges of the polynucleotide are neutralized by the polycation of the carrier). When using carriers made of polycations, such as polylysine, this ratio can be determined by standard gel retardation assay. After complexation of the carrier and polynucleotide, the polynucleotide binding agent-bacterial component conjugate is added to the reaction mixture to neutralize the remainder of the polynucleotide (see e.g., Wagner et al. (1992) PNAS 89:6099–6103).

The soluble molecular complex of the present invention can be used to selectively deliver polynucleotides to a target cell under a variety of conditions. For in vitro delivery of a polynucleotide, cultured cells can be incubated with the soluble molecular complex of the invention in an appropriate medium under conditions conducive to endocytotic uptake by the cells. The molecular complex can also be used ex vivo to enhance delivery of polynucleotides to cells or tissues which have been removed from an organism and will subsequently be returned to the organism.

For in vivo delivery of a polynucleotide, the molecular complex of the invention can be administered to an organism in a pharmaceutically acceptable vehicle. The term "pharmaceutically acceptable vehicle", as used herein, is intended to include any physiologically acceptable vehicle for stabilizing the soluble molecular complex of the present invention for administration in vivo, including, for example, saline and aqueous buffer solutions. The use of such media for pharmaceutically active substances is well known in the art. Except insofar as any conventional media is incompatible with the molecular complex of the present invention, use thereof in a therapeutic composition is contemplated.

The soluble molecular complex can be administered parenterally. Preferably, it is injected intravenously. Pharmaceutical compositions suitable for injectable use include sterile aqueous solutions. In all cases, the composition must be sterile and must be fluid to the extent that easy syringability exists. It must be stable under the conditions of manufacture and storage and must be preserved against the contaminating action or microorganisms such as bacteria and fungi.

This invention is illustrated further by the following examples which should not be construed as further limiting the subject invention. The contents of all references and published patent applications cited throughout this application are hereby incorporated by reference.

EXAMPLES

Example 1: Formation of a Soluble Molecular complex

A soluble soluble molecular complex for delivering plasmid DNA encoding the luciferase reporter gene from the firefly *Photinus pyralis* to cultured Huh-7 cells was produced as follows.

(a) Purification of Listeriolysin O (LLO)

LLO was purified according to the method of Geoffroy et al. (1987) *Infection & Immunity* 55:1641. In brief, Listeria monocytogenes strain 10403 S (kindly provided by Dr. Portnoy from U. Pennsylvania) was propagated in iron-free media. Culture supernatant was concentrated via pressure ultrafiltration at 4° C. using PM membrane (Amicon). Thiolpropyl Sepharose 4B or 6B columns were used to eliminate proteins that had no sulfhydryl group. The final product was purified through a Toyopearl HW-50 gel filtration column. Products from each purification step were tested for hemolytic activity according to the method of Geoffroy et al. (supra) and protein concentration to determine the percentage of recovery. Purity of proteins from each step was checked by SDS-PAGE.

(b) Formation of the Carrier: Coupling Asialoorosomucoid (ASOR) With Polylysine (PL)

ASOR-PL carrier was formed by chemically linking ASOR, labeled with iodine-125, to PL via a peptide bond. The linkage was formed with a water soluble carbodiimide as described by Jung, G. et al. (1981) *Biochem. Biphys. Res. Commun.* 101:599–606. The carrier was puff fled by molecular sieve chromatography.

(c) Linking LLO to the Carrier

In order to couple LLO to the ASOR-PL carrier, the carrier was first thiolated by incubating at neutral pH for 30 minutes with SPDP [N-Succinimidyl 3-(2-pyridyldithio) propionate], a heterobifunctional cleavable crosslinker which reacts with primary mines contained on either ASOR or PL (Cumber et al Meth Enzymol (1985) 112:207). Briefly, to 10 mg of ASOR-PL in 1 ml of borate buffered saline, 25 µl of a 20 mM solution of SPDP in DMSO was added. Unconjugated SPDP was removed by a PD-10 column.

Equal amounts of SPDP-ASOR-PL and LLO were then mixed to a total volume of 1 ml and reacted overnight at room temperature. The reaction mixture was then applied on a cation exchange HPLC system. The ASOR-PL-LLO conjugate was eluted with a continuous gradient of 20 mM sodium acetate (pH 5.1) to 20 mM sodium acetate plus 1 M sodium chloride (pH 5.1) for 40 minutes. The conjugate was eluted at the twelfth minute. The total eluent was 8 ml.

The amount of 2-pyridyl-disulfide introduced was determined by incubating the reaction product with dithiothreitol (DTT). The concentration of released pyridine-2-thione can be determined by measuring the absorbance at 343 mm (Molar extinction coefficient at 343 nm=$8.08 \times 10^3$ $M^{-1}$ $cm^{-1}$).

(d) Forming the Soluble Molecular Complex: Noncovalently Complexing the Polynucleotide and the ASOR-Polylysine-LLO Conjugate To determine the optimal proportion of ASOR-polylysine-LLO conjugate to DNA that yields a soluble complex, a gel retardation assay was performed. Briefly, increasing amounts of purified ASOR-polylysine-LLO conjugate were incubated in a 24 well dish for 30 minutes at room temperature with 2.0 µg/well of plasmid DNA, pCMVL (TargeTech, Inc.), which contains the gene for luciferase (De Wet et al. (1987) *Mol. Cell Biol.* 7(2) 725–737) driven by the CMV promoter/enhancer. This allows DNA complex to form in an electrostatic manner. Each sample was filtered through 0.45µ membranes to ensure that the complexes to be used were soluble.

Samples were then loaded on to an agarose gel for electrophoresis (see e.g., Wu et al. (1987) *J. Biol. Chem.* 262:4429–32). The proportion that completely retarded the migration of DNA in the gel was taken as the optimal ratio for complex formation.

Once the appropriate ratio of DNA to ASOR-PL-LLO had been determined, complexes were made up in large scale. Typically, 2 µg of plasmid DNA (in 0.9% saline) and 40 µg of ASOR-PL-LLO conjugate (in 0.9% saline) were mixed to a total volume of 20 µl and incubated at room temperature for 40 minutes to form the complex.

Example 2: In Vitro Transfection Assay Using the Soluble Molecular Complex

Soluble molecular complexes containing plasmid DNA, pCMVL (TargeTech, Inc.), were prepared according to the method described in Example 1. For transfection, complexes were then added to 500 µg of serum free Dulbecco's Modified Essential Medium (DMEM) with 2% calcium filtered through a 0.45µ Durapore membrane (Millpore Inc.) and added to cultured Huh-7 (asialoglycoprotein receptor (+))cells (Liang J. et al. (1993) *J. Clin. Invest.* 91:1241–1246). Control cells were transfected with ASOR-PL-pCMVL complex alone (prepared according to the method of Wu et al. (1988) *Biochemistry* 27(3):887) and with ASOR-PL-pCMVL complex and free Listefiolysin O.

The cells were incubated with the ASOR-PL-LLO-pCMVL complex for four hours at 37 ° C., then the medium was removed and replaced with fresh DMEM containing 10% fetal bovine serum. The incubation was continued for forty-eight hours. Cell lysates were assayed in triplicate for luciferase activity in light units using a luciferase gene expression detection kit (Promega). The results are shown in Table 1 and demonstrate that complexes containing LLO produced a greater than 100-fold increase in gene expression over complex alone or complex and free LLO, without any evidence of toxicity to cells. Exposure of cells to complexes and free LLO only produced a four fold increase in gene expression.

Exposure of ASOR-PL-LLO-pCMVL complexes to SKHep-1 (asialoglycoprotein receptor (–)) cells produced no significant expression under any conditions (see Table 2). This demonstrates that the complexes are internalized into cells by binding to asialoglycoprotein surface receptors which are then internalized into cells via endocytosis.

Competition assays using a 100 fold molar excess of free radio-labeled ASOR were then performed to determine the specificity of the ASOR-PL-LLO-pCMVL complex. The results are also shown in Table 1. The free ASOR effectively competed with the ASOR-PL-LLO-pCMVL complex, resulting in a 3-log decrease in activity. This showed that the ASOR-PL-LLO-pCMVL complex is very target specific (i.e., is taken up by ASOR receptors only).

TABLE 1

| Addition | Activity (Light Units/ 25 µg Cell Protein) |
|---|---|
| ASOR—PL—DNA Complex | 2,100 ± 1,180 |
| ASOR—PL—DNA Complex + free LLO | 9,780 ± 8,170 |
| ASOR—PL—DNA—LLO Complex | 223,440 ± 4,510 |
| ASOR—PL—DNA—LLO Complex + excess AsOR | 330 ± 9 |

TABLE 2

| Addition | Activity (Light Units/ 25 µg Cell Protein) | |
|---|---|---|
| | Huh-7 Cells | SKHep-1 Cells |
| ASOR—PL—DNA—LLO Complex | 90,195 ± 6,991 | 107 ± 18 |

Example 3: Endosomolytic Peptides of LLO

In this example, peptides of listeriolysin O (LLO) having pH-dependent hemolytic activity were identified.

LLO protein is homologous to streptolysin O and pneumolysin in terms of the protein sequence. A peptide of 11 areinc acids (ECTGLAWEWWR) (SEQ ID NO: 1) which are 100% conserved in these three proteins, contains a unique cysteine shown to be essential for the lytic activity (see. e.g. Mengaud et al. (1988) *Infection and Immunity* 56:766–772.) Therefore, to obtain peptides from LLO having lytic activity peptides containing this sequence were expressed and tested as follows.

A clone containing the entire coding region of LLO from a λt11 library of Listeria monocytogenes (purchased from Clonetech) was isolated using oligonucleotides of known LLO sequences as hybridization probes. A 201 base pair fragment of this clone containing the putative active hemolytic domain (i.e., the domain encoding the areinc acid sequence ECTGLAWEWWR (SEQ ID NO: 1) was then subcloned into the bacterial expression vector, pGEX-2X (obtained from Pharmacia Biotech). Purification of the resultant GST-LLO fusion protein was accomplished by binding of the GST tag to agarose beads containing glutathione. A thrombin protease site allowed subsequent cleavage of the GST domain from the LLO portion of the protein.

In order to test the expressed domain of LLO for lytic activity, hemolytic assays were performed on bacterial extracts containing the GST-LLO fusion protein and on the purified fusion protein as follows:

Blood (5 mls) was dram into a purple tube (3.5% citrated tubes) and spun at 1000 rpm for 5 minutes. Serum/plasma was then removed from the sample and red blood cells (RBC) were washed two times with PBS, pH 7.0. An aliquot of 2 µl was taken and cells were counted in a hemocytometer. The total number of cells for the 15 µl RBC sample was measured to be approximately $10^8$ RBC.

The 15 p-1RBC sample was then combined with 1 ml of PBS, pH 6.0 or 7.0. A 5 µl sample of the bacterial extract or purified GST-LLO fusion protein was then added to 15 µl of the RBC sample. A 5 µl aliquot of the RBC sample was used as a negative control. A 15 µl aliquot of the RBC sample, to which 1 ml of $H_2O$ was added, was used as a positive control.

5 µl of 1 M DTT, a reducing agent, (final DTT=5mM) was then added to the test samples and the samples were gently mixed by tapping the side of the tubes. Tubes were visually checked to ensure mixing of RBCs. Samples were incubated in a 37° C. bath for 30–60 minutes, and then centrifuged at 1000 rpm for 5 minutes.

Samples were checked visually for cell lysis (red supt). Alternatively, optical density (OD) measurements could have been taken at A530 nm.

Results

Bacterial extracts containing the GST-LLO fusion protein were positive for lysis of red blood cells. Purified fusion protein also had hemolytic activity, indicating that the activity was not due to some component in the bacterial extract. Extracts from bacteria producing only the GST portion of the fusion protein were negative for hemolytic activity, suggesting that the activity was due to the LLO portion of the fusion protein.

These results demonstrate that fragments of LLO having lytic activity (i.e., the ability to lyse cells or endosomes) can be recombinantly produced. These fragments of LLO can then be incorporated into the molecular complex of the invention, as described in Example 1, in place of the full-length LLO protein.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A soluble molecular complex for targeting a polynucleotide to a specific cell comprising:
   a) a polynucleotide;
   b) a carrier comprised of a polynucleotide binding agent and a cell-specific binding agent which binds to a surface molecule of the cell and is internalized into an endosome; and
   c) a bacterial component which lyses the endosome resulting in release of the polynucleotide into the cytoplasm of the cell.

2. The soluble molecular complex of claim 1, wherein the polynucleotide is DNA.

3. The soluble molecular complex of claim 1, wherein the polynucleotide comprises a gene linked to genetic regulatory elements required for expression of the gene product by the target cell.

4. The soluble molecular complex of claim 1, wherein the polynucleotide is an antisense oligonucleotide.

5. The soluble molecular complex of claim 1, wherein the polynucleotide is a ribozyme directed against an RNA in the cell.

6. The soluble molecular complex of claim 1, wherein the polynucleotide binding agent is polylysine.

7. The soluble molecular complex of claim 1, wherein the cell-specific binding agent is an asialoglycoprotein.

8. The soluble molecular complex of claim 1, wherein the bacterial component is activated upon internalization into the endosome.

9. The soluble molecular complex of claim 1, wherein the bacterial component is pH dependent.

10. The soluble molecular complex of claim 1, wherein the bacterial component is thiol-activated.

11. The soluble molecular complex of claim 1, wherein the bacterial component is listeriolysin O.

12. A soluble molecular complex for targeting a polynucleotide to a specific cell comprising:
    a) a polynucleotide;
    b) a carrier comprised of polylysine and an asialoglycoprotein; and
    c) listeriolysin O.

13. The soluble molecular complex of claim 12, wherein the listeriolysin O is linked to the carrier by a disulfide bond.

14. A composition comprising the molecular complex of claim 1 and a carrier solution.

15. A soluble molecular complex for targeting a polynucleotide to a specific cell comprising:
    a) a polynucleotide;
    b) a carrier comprised of a polycation which noncovalently binds the polynucleotide and a cell-specific binding agent; and
    c) a fragment of a bacterial component having endosomolytic activity.

16. The complex of claim 15, wherein the bacterial component is listeriolysin O.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 11 amino acids
        ( B ) TYPE:AMINO
        ( B ) TYPE:AMINO
        ( C ) TOPOLOGY: linear -continued (ii) MOLECULE TYPE: peptide (xi) SEQUENCE DESCRIPTION: SEQ ID NO:1:

```
Glu Cys Thr Gly Leu Ala Trp Glu Trp Trp Arg
 1               5                  10
```